United States Patent [19]

Lyell

[11] Patent Number: 4,985,038
[45] Date of Patent: Jan. 15, 1991

[54] NEEDLE STOP SURGICAL INSTRUMENT

[76] Inventor: Mark S. Lyell, 2024 Barryton Rd., Oklahoma City, Okla. 73120

[21] Appl. No.: 533,529

[22] Filed: Jun. 5, 1990

[51] Int. Cl.⁵ ............................................. A61B 17/04
[52] U.S. Cl. ............................................ 506/148; 2/21
[58] Field of Search .............. 606/148; 2/21; 223/101; 294/25

[56] References Cited

U.S. PATENT DOCUMENTS

| | | | |
|---|---|---|---|
| 1,380,960 | 6/1921 | Hmenia | 223/101 |
| 2,462,208 | 2/1949 | Meyer | 294/25 |
| 2,588,528 | 3/1952 | Howser | 223/101 |
| 2,781,760 | 2/1957 | Baer | 606/167 |
| 2,811,969 | 11/1957 | Shubert | 606/125 |
| 2,847,012 | 8/1958 | Eastman | 606/125 |
| 3,228,033 | 1/1966 | Ames et al. | 2/21 |
| 3,511,242 | 5/1970 | Agnone et al. | 606/148 |
| 3,735,760 | 5/1973 | Vreeland, Jr. | 606/125 X R |

Primary Examiner—Ronald Frinks
Attorney, Agent, or Firm—Wenderoth, Lind & Ponack

[57] ABSTRACT

A needle stop surgical instrument comprising a finger housing, a needle receiving space, and a handle. The finger housing is adapted for receiving a finger. At one end of the finger housing is an endwall for protecting the finger from injury and the needle receiving space for receiving and guiding a needle. The needle receiving space is preferably in the shape of a cone. At the opposite end of the finger housing is connected the handle which is designed such that when a finger is received in the housing, the remaining fingers of the hand can grip the handle.

The instrument is used in a Stamey procedure or similar procedures. The needle stop is used to protect a surgeon's finger from risk of needle injury, by being capable of receiving and guiding a needle through a surgical incision. Using the needle stop, a surgeon can avoid the risk of contracting serious infectious diseases, such as AIDS and Hepatitis B.

9 Claims, 2 Drawing Sheets

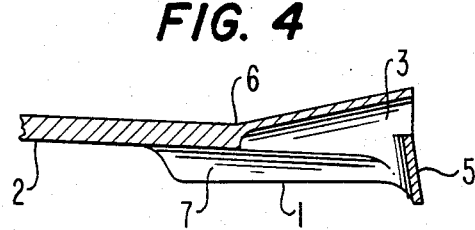
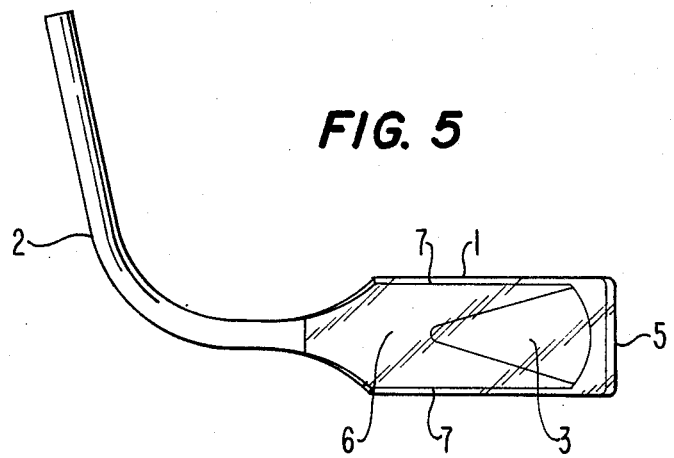

NEEDLE STOP SURGICAL INSTRUMENT

This invention relates to a surgical instrument for receiving and guiding a needle during a surgical procedure. More particularly, the invention is a needle stop device for receiving and guiding a surgical needle during a Stamey procedure and similar procedures. The instrument is designed to protect the surgeon from needle injury during the procedure, and consequently to protect the surgeon from the risk of infection from Acquired Immune Deficiency Syndrome (AIDS), Hepatitis, and other diseases.

BACKGROUND OF THE INVENTION

1. Field of the Invention

The Stamey procedure is a surgical procedure for the treatment of stress urinary incontinence in women. Another similar procedure is the Pereyra procedure. The Stamey procedure involves placing sutures in the periurethral tissue at the bladder neck. These sutures are passed up to the rectus fascia with the Stamey needle. The sutures are used to elevate the bladder neck to help restore continence. A vaginal incision is made which permits the surgeon to rest a finger against the neck of the bladder. The Stamey needle is passed through the rectis fascia posterior to the symphysis pubis and advanced along the posterior surface of the symphysis.

It is the present practice for the surgeon to locate the position of the needle in the pelvis by inserting the index finger of the surgeon's nondominant hand into the vaginal incision at the ipsilateral bladder neck and by moving the point of the needle onto the tip of the surgeon's index finger with the surgeon's other hand. The surgeon's index finger is kept on the needle point as the needle is guided through the pelvis and out through the vaginal incision. For a complete description of the Stamey procedure, the reader is referred to Campbell's Urology, Fifth Edition, pages 2702-2710.

One of the hazards of this procedure is laceration or puncture of the surgeon's index finger by the needle. Before the prevalence of Hepatitis B and AIDS, the risk of infection was minimal. However, due to the serious nature of these and similar diseases, it is now mandatory for the surgeon to protect himself or herself and the patient by preventing the occurrence of needle lacerations or punctures during these procedures. Using the needle stop of my invention, this hazard is eliminated.

2. Description of the Prior Art

Various instruments have been known heretofore for protecting one's finger from needle injury. U.S. Pat. No. 3,228,033 to Ames et al. relates to a finger guard for protecting the fingers of a person from injury from a baby diaper pin. U.S. Pat. No. 3,511,242 to Agnone relates to a surgical finger cot for protecting the fingers of a surgeon from injury from a suturing needle, which finger cot is flexible enough to feel and support a patient's damaged tissue during surgery. U.S. Pat. No. 1,380,960 to Hmenia relates to a thimble for protecting the finger from injury from a crocheting needle.

Other surgical instruments have been known which include a finger housing or glove. U.S. Pat. No. 2,781,760 to Baer relates to a instrument for mitral valve surgery containing a crescentic blade, which instrument is adapted for fitting onto a surgeon's index finger. U.S. Pat. No. 2,847,012 to Eastman relates to a surgical glove for rupturing amniotic membranes. U.S. Pat. No. 2,811,969 to Schubert relates to another obstetrical instrument for rupturing the amniotic sac.

However, the instruments of these types are limited in in the degree of control they offer for receiving and guiding a needle through an incision, or in the degree of protection they afford a surgeon from needle injury.

SUMMARY OF THE INVENTION

I have now devised a surgical instrument which is designed to assist a surgeon in the performance of a Stamey procedure and similar procedures by receiving and guiding the needle during the surgical procedure, while at the same time protecting the surgeon from needle injury.

The needle stop of my invention is a hand-held instrument composed of three main parts: a finger housing, a needle receiving space, and a handle. The finger housing is adapted for receiving a finger. At one end of the finger housing is connected the needle receiving space for receiving and guiding a needle. At the opposite end of the finger housing is connected the handle which is designed such that when a finger is received in the housing, the remaining fingers of the hand can grip the handle.

The instrument is used in the portion of the Stamey procedure in which the Stamey needle is passed posterior to the symphysis pubis. The surgeon inserts a finger, preferably the index finger of the surgeon's nondominant hand, into the finger housing of the needle stop and grasps the handle with the other fingers. The needle stop is then inserted into the vaginal incision and advanced posterior to the symphysis. The Stamey needle is then advanced with the surgeon's other hand into the needle receiving space of the needle stop. With the needle in the needle stop, the needle can then be directed through the pelvis and out through the vaginal incision without risk of injury to the surgeon.

These and other novel features of the needle stop of my invention will be more readily understood by reference to the accompanying drawings, of which the following is a brief description.

BRIEF DESCRIPTION OF THE DRAWINGS

FIG. 4 is a cross-sectional view thereof taken along line 4—4 of FIG. 3; and

FIG. 5 is a top plan view of another embodiment of my invention, wherein the finger housing has a top portion to completely enclose a finger inserted in the finger housing.

DESCRIPTION OF THE PREFERRED EMBODIMENTS

Figure 1:
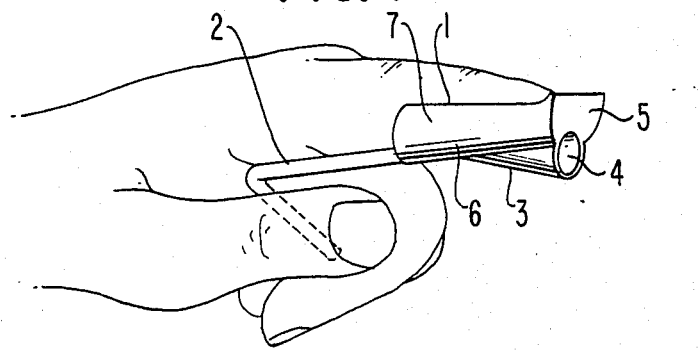
FIG. 1 is a perspective view showing the needle stop surgical instrument of my invention and how it is held by a hand for use.
Figure 2:
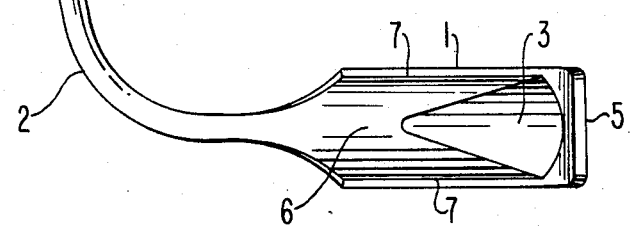
FIG. 2 is a top plan view thereof.
Figure 3:
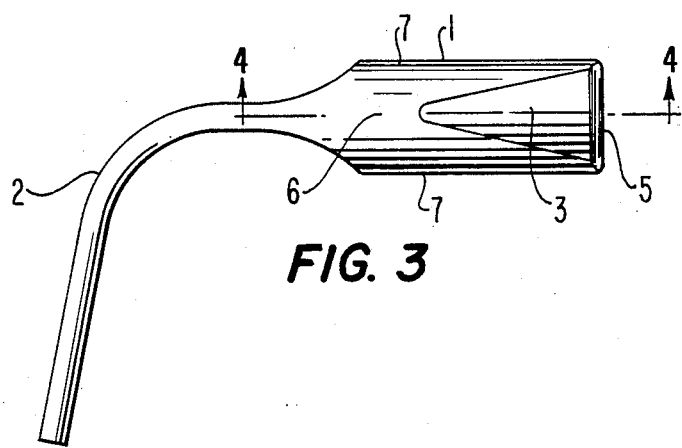
FIG. 3 is a bottom plan view thereof.

As shown in FIG. 1, the needle stop surgical instrument of my invention comprises a finger housing 1 for receiving a finger. A handle 2 is connected to one end of the finger housing, the handle being designed such that when one finger of a hand is received in the housing, the remaining fingers of the hand can grip the handle. Connected to the finger housing is a needle receiving space 3 having an opening 4 for receiving a needle therethrough.

The finger housing has, at the end opposite the handle, an endwall 5 for protecting the finger, which is received in the finger housing, from needle injury. Extending from the endwall to the handle of the finger housing is a base portion 6 for receiving the finger thereagainst, as well as sidewalls 7 extending along the base portion from end to end. The base portion, endwall and sidewalls of the finger housing together define a finger receiving space having an interior surface.

The needle receiving space is connected to the finger housing at the end of the finger housing proximate to the endwall of the housing. The needle receiving space comprises a portion of the exterior surface of the finger housing and a space-defining wall member connected thereto. The needle receiving space is substantially in the shape of a cone, with the open base of the cone forming the opening for receiving a needle. The needle receiving space is also tapered at the open base end to avoid tissue laceration.

The handle extends from the finger housing along the longitudinal axis of the finger housing and along a first section which is grippable between the index finger received in the finger housing and the thumb of the hand of the index finger. The handle then extends at an angle from the first section along a second section which is grippable between the remaining fingers of the hand and the palm of the hand.

FIG. 5 shows another embodiment of the needle stop of my invention, wherein the finger housing has a top portion attached to the upper edge surfaces of the sidewalls and endwall of the finger housing to form a hollow finger receiving space, so as to completely enclose a finger inserted into the finger housing. The top portion helps to support and retain a finger in the finger housing.

The needle stop of my invention can be made in a variety of sizes, and in right-handed as well as left-handed models. With respect to the dimensions of the instrument shown in the figures, the finger housing has a total length of 5 cm and an outside diameter of 1.5 cm. The handle is approximately 13 cm in total length, of which the first section is 4 cm and the second section is 9 cm, and it is 0.5 cm in outside diameter. The needle receiving space has a circular opening of 1.5 cm in diameter and a depth of 3 cm.

The needle stop of my invention can be made from any suitable material which is sufficiently rigid and which will not be punctured by a needle, e.g., plastic, metal, etc. Preferably, the needle stop is composed of stainless steel. Alternatively, the needle stop can be formed of materials such that it can be used as a disposable instrument, e.g., the needle receiving space can be made of stainless steel and the finger housing made of a plastic or other synthetic material. The handle can be formed of any rigid material, however, preferably, it is a maleable material which the user can bend to a comfortable position, e.g., a plastic coated wire or soft metal. The top portion of the finger housing, as shown in the embodiment of FIG. 5, is composed of a transparent resilient material. However, the top portion is not restricted to this material, but it can be composed of other types of flexible or resilient materials, or even a rigid material such as the same material composing the finger housing, such that the finger housing can be formed in one piece. The top portion is seen to help support and retain a finger, and fingers of different sizes, which are inserted in the housing.

It is also conceived that the needle receiving space can include a means for retaining and holding a needle inserted therein.

Using the needle stop of my invention, a surgeon can protect his or her finger from needle laceration or puncture during a Stamey or similar procedure, thus eliminating the risk of contracting a serious infectious disease like Hepatitis B or AIDS.

While specific details of the needle stop and particular materials have been referred to in describing the embodiments illustrated above, it will be understood that other details of construction and other materials may be resorted to within the spirit of the invention.

I claim:

1. A needle stop for receiving and guiding a needle during surgical procedures, comprising:
   a finger housing for receiving a finger therein;
   a handle connected to one end of said finger housing, said handle designed such that when one finger of a hand is received in said housing, the remaining fingers of the hand can grip said handle; and
   means connected to said finger housing defining a needle receiving space for receiving and guiding a needle, said space having an opening for receiving a needle therethrough.

2. The needle stop as set forth in claim 1, wherein:
   said finger housing has a second end opposite said one end, and an endwall at said second end for protecting a finger received in said finger housing.

3. The needle stop as set forth in claim 2, wherein:
   said finger housing has a base portion for receiving a finger thereagainst extending from said endwall at said second end to said one end and sidewalls extending along said base portion from said endwall to said one end.

4. The needle stop as set forth in claim 3, wherein:
   said base portion, said endwall and said sidewalls of said finger housing together define a finger receiving space having an interior surface; and
   said means defining a needle receiving space is connected to said finger housing on an exterior surface thereof.

5. The needle stop as set forth in claim 3, wherein:
   said finger housing has a top portion extending along said sidewalls from said endwall at said second end to said one end, and
   said base portion, said endwall, said sidewalls and said top portion of said finger housing together define a finger receiving space having an interior surface.

6. The needle stop as set forth in claim 1, wherein:
   said means defining a needle receiving space comprises a portion of the exterior surface of said finger housing and a space-defining wall member connected thereto.

7. The needle stop as set forth in claim 6, wherein:
   said needle receiving space is substantially in the shape of a cone, the base of said cone forming said opening for receiving a needle.

8. The needle stop as set forth in claim 7, wherein:
   said portion of said exterior surface of said finger housing is partially conical; and
   said space defining wall member is partially conical.

9. The needle stop as set forth in claim 1, wherein:
   said handle connected to said one end of said finger housing extends from said finger housing along substantially the longitudinal axis of said finger housing along a first section thereof so as to be grippable between an index finger received in said finger housing and the thumb of the hand of the index finger, and then extends at an angle from said first section along a second section thereof so as to be grippable between the remaining fingers of the hand and the palm of the hand.

* * * * *